(12) United States Patent (10) Patent No.: US 9,141,834 B2
Lautzenhiser et al. (45) Date of Patent: Sep. 22, 2015

(54) ULTRASONIC IDENTIFICATION OF REPLACEABLE COMPONENT FOR HOST SYSTEM

(71) Applicants: Frans Lautzenhiser, Zionsville, IN (US); James Dallas, Superior, CO (US)

(72) Inventors: Frans Lautzenhiser, Zionsville, IN (US); James Dallas, Superior, CO (US)

(73) Assignee: Piezotech LLC, Indianapolis, IN (US)

( * ) Notice: Subject to any disclaimer, the term of this patent is extended or adjusted under 35 U.S.C. 154(b) by 72 days.

(21) Appl. No.: 13/911,731

(22) Filed: Jun. 6, 2013

(65) Prior Publication Data

US 2013/0327827 A1 Dec. 12, 2013

Related U.S. Application Data

(60) Provisional application No. 61/656,376, filed on Jun. 6, 2012.

(51) Int. Cl.
*G06K 19/06* (2006.01)
*G06K 7/04* (2006.01)
*G05B 19/12* (2006.01)
*G06K 7/02* (2006.01)

(52) U.S. Cl.
CPC .............. *G06K 7/042* (2013.01); *G05B 19/126* (2013.01); *G06K 7/02* (2013.01)

(58) Field of Classification Search
CPC . G06K 17/00; G06K 19/06037; G05B 19/126
USPC .................. 235/375, 435, 439, 487, 490, 494
See application file for complete search history.

(56) References Cited

U.S. PATENT DOCUMENTS

| | | | |
|---|---|---|---|
| 3,703,625 A | 11/1972 | Urbin | |
| 5,168,477 A * | 12/1992 | Schenato et al. | 367/87 |
| 5,608,199 A * | 3/1997 | Clouse et al. | 235/435 |
| 5,773,811 A | 6/1998 | Schramm | |
| 6,626,355 B2 * | 9/2003 | Sasse et al. | 235/375 |
| 7,661,582 B2 * | 2/2010 | Mollstam | 235/375 |
| 8,009,015 B2 * | 8/2011 | Sayers et al. | 340/5.64 |
| 8,210,178 B2 * | 7/2012 | Schermeier et al. | 128/205.28 |
| 8,257,299 B2 * | 9/2012 | Childers et al. | 604/29 |
| 8,746,547 B2 * | 6/2014 | Mollstam et al. | 235/375 |
| 2001/0020148 A1* | 9/2001 | Sasse et al. | 604/65 |
| 2006/0058804 A1* | 3/2006 | Mollstam | 606/80 |
| 2006/0131329 A1* | 6/2006 | Sayers et al. | 222/105 |
| 2006/0181421 A1 | 8/2006 | Forcier | |
| 2006/0278220 A1* | 12/2006 | Schermeier et al. | 128/203.12 |
| 2010/0155465 A1* | 6/2010 | Mollstam et al. | 235/375 |
| 2010/0324423 A1 | 12/2010 | El-Aklouk | |
| 2011/0253787 A1 | 10/2011 | Melands | |
| 2012/0074305 A1 | 3/2012 | Scholes | |
| 2012/0089085 A1* | 4/2012 | Childers et al. | 604/29 |

* cited by examiner

*Primary Examiner* — Paultep Savusdiphol
(74) *Attorney, Agent, or Firm* — Overhauser Law Offices LLC

(57) ABSTRACT

A system, method and device are provided for detecting the presence of, and/or obtain information about, a replaceable component for a host system. A host system has an ultrasonic transducer pair that detects the presence of, and/or obtains information about, a replaceable component for a host system through receipt or non-receipt of an ultrasonic signal. The replaceable component includes a key or other feature that either allows the transmission of a transmitted ultrasonic signal, or which does not allow the reception of the transmitted ultrasonic signal, depending on the host configuration.

25 Claims, 16 Drawing Sheets

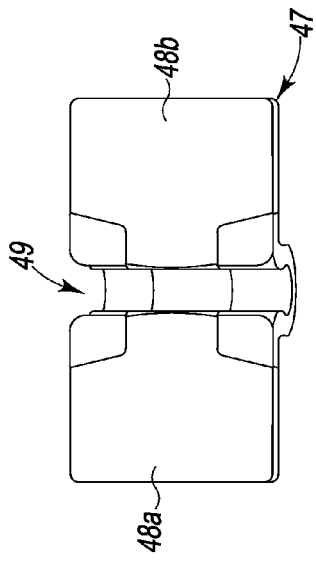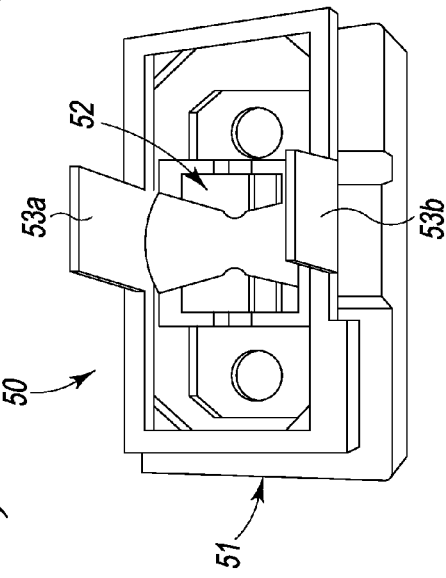
Fig. 4A (Prior Art)
Fig. 4B (Prior Art)
Fig. 4C (Prior Art)

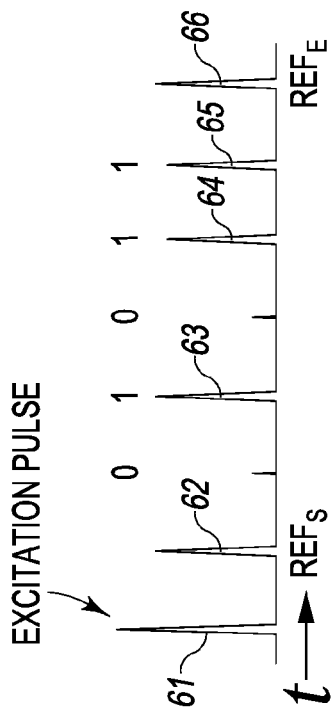
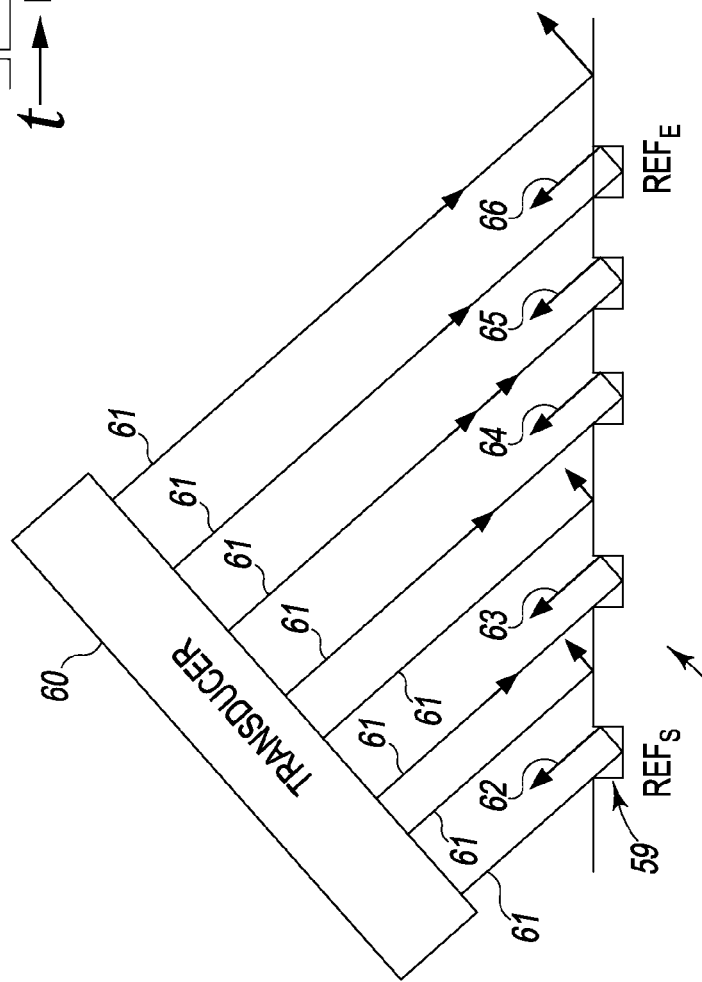
Fig. 5B
Fig. 5A

ULTRASONIC IDENTIFICATION OF REPLACEABLE COMPONENT FOR HOST SYSTEM

CROSS-REFERENCE TO RELATED APPLICATIONS

This US non-provisional patent application claims the benefit of and priority to U.S. provisional patent application Ser. No. 61/656,376 filed Jun. 6, 2012 entitled "Ultrasonic Identification of Replaceable Component For Host System", the entire contents of which is specifically incorporated herein by reference.

FIELD OF THE INVENTION

The present invention relates to the field of ultrasonic transducers and, more particularly, to ultrasonic transducers used for identification.

BACKGROUND

Numerous host systems utilize replaceable components that are held by a receptacle of the host system. Examples include a military aircraft that uses replaceable missiles or other projectiles, or a medical infusion pump that receives cassettes with tube sets for facilitating the delivery of fluids to a patient. Host systems may also include items that receive replaceable batteries, memory cards and the like. A common feature of such host systems is that they include a receptacle shaped to allow it to receive a replaceable component having cooperating shape. For example, military aircraft may have missile launch tubes 4 inches in diameter to receive either air-to-air missiles or rocket-propelled grenades, either of which may be sized for a four inch tube. A medical infusion pump may be shaped to receive a cassette that holds fluid delivery tubing of various diameters or sizes. A flashlight may be sized to receive batteries of various sizes, such as AA, AAA, C or D and the like.

Host systems also frequently alter their functionality depending on either the presence or type of replaceable component in the receptacle of the host system. For example, for a medical infusion pump, if a tubing cassette is not detected, it may be desirable to indicate a fault condition, such as by flashing a red light our sounding an audible alarm.

Host systems having a receptacle usually interact with a replaceable component some way lithe replaceable component is a battery, the host system may receive electrical energy from the battery. Some host systems, such as medical infusion pumps, interact with the tubing within a tubing cassette via ultrasonic sensors to monitor fluid flowing through the tubing. A military aircraft may interact with a replaceable component such as a missile by both launching the missile, and by reading information about the particular type of missile held by the aircraft.

In addition to detecting the presence or absence of a replaceable component, it is sometimes desirable to obtain information about the replaceable component held by the host system. The types of information it may be desirable to obtain about the replaceable component may be information regarding its operating characteristics (size, power, etc.) or its authenticity, i.e., whether it is genuine or counterfeit. This is particularly important for replaceable components designed for highly specialized host systems, such as medical infusion pumps. For example, the performance of tubing cassettes for medical infusion pumps depend their adherence to exacting tolerances and standards. Unfortunately, poor quality replacement components are often manufactured by other companies that pay little attention to the performance of the component, but only to ensuring that it is sized to fit into the host system.

The present disclosure is directed toward host systems that have an ultrasonic transducer that detects the presence of, and/or obtains information about, a replaceable component for a host system.

For example, military aircraft may be armed with rockets contained in pods for rapid firing. Each pod may carry 7 to 19 rockets. Since the rockets may have been loaded under extreme stress, or at night, or in inclement weather, or on a carrier or other ship engaged in battle, a manual inventory may not be possible or accurate. Thus, a pilot may not know which of several possible warhead types are available to fire.

A variety of optical or electromagnetic systems for identifying warheads in an aircraft launch tube have been evaluated. Such systems have not proven reliable, particularly under the high-stress, high-temperature, small-space conditions of a military aircraft.

A need therefore exists for a device and method that permits pilots to determine from the cockpit what rockets are loaded in their aircraft launch tubes. The present invention addresses that need.

Similarly, a need exists for a medical infusion pump to be able to ascertain the presence and characteristics of a tubing cassette capable of being held by the pump.

SUMMARY OF THE INVENTION

There is presently disclosed a system, device and method for identifying a replacement component of a host system.

One system, device and method includes:
a) providing a pattern of grooves on the surface of the replaceable component, with the pattern of grooves being associated with an identification code identifying the replaceable component or a characteristic, of the replaceable component;
b) placing the replaceable component in the receptacle of the host system;
c) providing a piezoelectric transducer on the host system;
d) emitting an ultrasonic wave from the piezoelectric transducer to the pattern of grooves, wherein the wave encounters the pattern of grooves at an angle of less than 90° so that waves striking the interior of a groove are reflected back to the transducer as echo waves, while waves not striking the interior of a groove are reflected away from the transducer, and
e) reading the pattern of returning echo waves to determine the identification code indicated by the pattern of grooves on the replaceable component.

Another embodiment of the invention involves:
a) providing a replaceable component receptacle of host system with a piezoelectric transmitter and a piezoelectric receiver that has a gap between them, and wherein the replaceable component receptacle is shaped to receive a replaceable component having an element that is between the gap when the replaceable component is received by the receptacle;
b) emitting an ultrasonic signal from the piezoelectric transmitter; and
c) detecting whether the emitted ultrasonic signal is received by the piezoelectric receiver.

Another embodiment of the invention involves:
a) a replaceable component for a host system;
b) wherein, the host system includes
1) a receptacle; and 2) a piezoelectric transmitter and a piezoelectric receiver spaced from the piezoelectric transmitter to form a gap between them, c) wherein the replaceable component is shaped to complete an ultrasonic pathway between the piezoelectric transmitter and the piezoelectric receiver when the replaceable component is inserted into the receptacle;

d) emitting an ultrasonic signal from the piezoelectric transmitter;

e) detecting whether the emitted ultrasonic signal is received by piezoelectric receiver to ascertain whether the replaceable component is received in the receptacle.

Another embodiment of the invention involves;

a) providing a replaceable component receptacle of host system with a piezoelectric transducer positioned to transmit an ultrasonic signal toward a replaceable component received by the receptacle, and wherein the replaceable component has a surface oriented to reflect an ultrasonic signal transmitted by the piezoelectric transducer back to the piezoelectric transducer;

b) emitting an ultrasonic signal from the piezoelectric transducer; and c) detecting the presence or absence of a reflected ultrasonic signal to determine the presence, or a type or characteristic, of the replaceable component.

BRIEF DESCRIPTION OF THE DRAWINGS

FIGS. 4A-C are illustrations of various prior art, single tube pump configurations FIG. 5A is an illustration of an embodiment of the invention.

FIG. 5B is an illustration of a returning echo pattern of the groove pattern of FIG. 5A.

Like reference numbers indicate the same or similar parts throughout the several figures.

DESCRIPTION OF THE INVENTION

Figure 1:
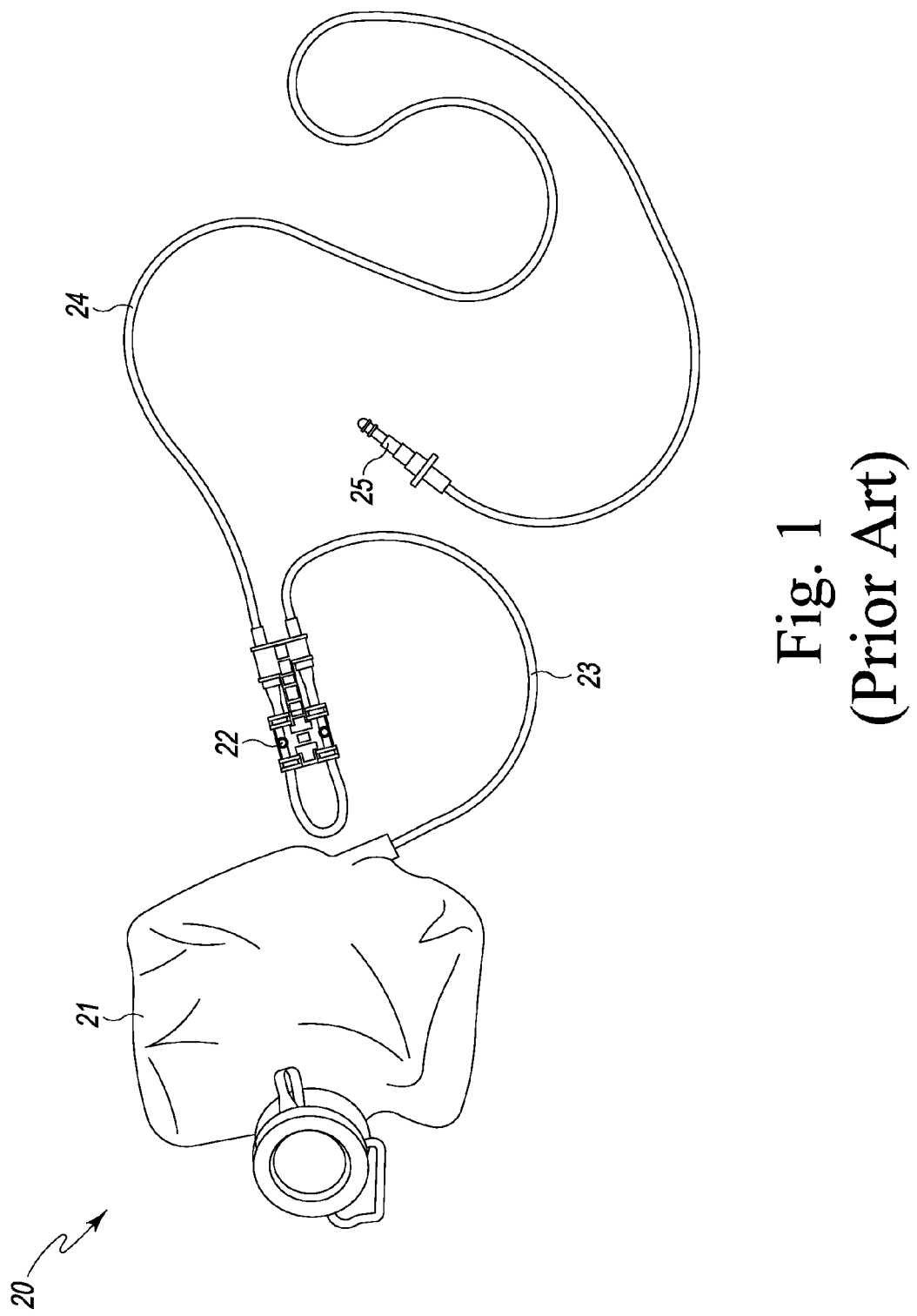
FIG. 1 is a plan view of a prior art medical IV tubing set.

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Presently disclosed is a device and method for detecting an identification (ID) code pattern machined, stamped or otherwise formed on the surface of an object such as a military warhead loaded in an aircraft rocket launch tube. Preferably, a single ultrasonic transducer is provided at a substantially fixed position with respect to the ID pattern, and an ultrasonic wave is pulsed against the pattern. The returning echo waves are received and read to determine the ID pattern on the object.

A typical pattern may include a set of parallel grooves having a known, repetitive spacing. At each spacing interval a groove may or may not be present. For example, the presence of a groove may be associated with the number "1," and the absence of a groove may be associated with the number "0". A pattern of grooves can then in that manner indicate a simple binary number.

The binary number can be detected using a short pulse of ultrasound. To accomplish this, the transducer is oriented so that a pulse from the transducer strikes the pattern at an appropriate angle from above the pattern. In the plane of the pattern the ultrasound strikes the grooves at a perpendicular angle. The profile of the grooves is such that ultrasound that strikes a groove will be reflected back to the transducer. If a groove is not present the ultrasound will be reflected away from the transducer.

Echoes returning from the pattern are separated in time, with echoes from progressively more distant grooves returning at a progressively later time. By time gating the returning echoes it is possible to derive a simple binary number, or code.

One advantage of the present invention is that it provides a way for a military pilot to quickly generate an inventory and store it automatically into a computer after the rockets are loaded into the pod. No member of the crew needs to do a time consuming, manual inventory of the rockets.

The simplicity of the system is also an advantage. Only one single-element ultrasonic transducer is required to read the warhead ID tag if all warheads are similarly sized. Additionally, only one coaxial cable is required per transducer. In embodiments in which rockets of different lengths may be loaded, each tube in the pod may require two or more transducers to accommodate rockets of different lengths. This contrasts to systems in which arrays of transducers are used for each warhead. In that case, many more transducers and cables may be required.

FIG. 5A shows an embodiment of the inventive device. In FIG. 5A, grooves 59 are cut perpendicularly to the surface of the object to be identified, with the illustrated grooves having a "rectangular" or "box cut" shape.

The groove pattern 58 in FIG. 5A begins with a "start" reference groove ($REF_S$), and ends with an "end" reference groove ($REF_E$). The "start" and "end" reference grooves indicate to the ID reader that the pattern is beginning and ending, respectively. The grooves between the "start" and "end" reference grooves are therefore understood by the reader to contain identification information.

As discussed above, the transducer 60 is positioned above the surface at an angle such that ultrasonic beam/signal 61 intercepts the grooves 59 at an angle. Beams/waves that enter a groove are reflected back 62 to the transducer, while beams/grooves that do not enter a groove are reflected away. The travel time of the ultrasonic waves reflected back from the closest grooves is shorter, while the travel time of the ultrasonic waves reflected back from the grooves further away is slightly longer.

If no groove is present, the ultrasound striking the pattern in that region is deflected away from the transducer 60. If a groove 59 is present the sound is reflected back to the transducer 60 at the same angle as the incident wave.

Accordingly, it can be seen that FIG. 5B shows the returning echo pattern and the binary number (01011) for the groove pattern shown. The excitation pulse 61 triggers the start reference reflection/echo 62 and reflections/echoes 63, 64, 65 and end reference signal 66 to form the binary number (01011).

The groove profile may be modified to enhance performance. If the incident wave angle and direction is known, the groove may be modified as shown in FIG. 6 or FIG. 7.

Figure 6:
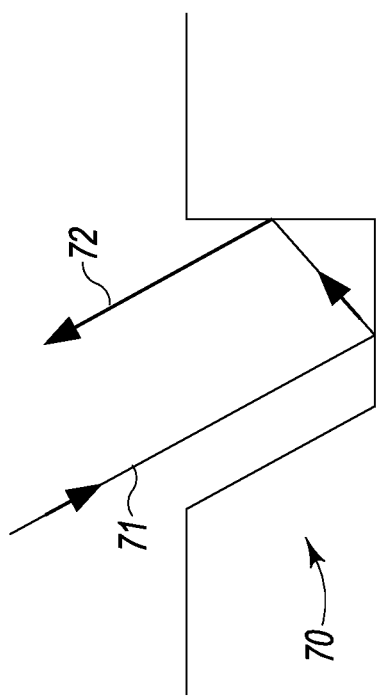
FIG. 6 is an alternative groove shape that may be used in embodiments of the present invention.

FIG. 6 shows an alternative groove shape 70 that may be used in other embodiments of the present invention. In FIG. 6, the leading face of each groove 70 is "cut" or angled rather than being perpendicular to the surface of the object. The incoming ultrasonic signal 71 is reflected by the groove shape 70 to provide the ultrasonic reflection 72.

Figure 7:
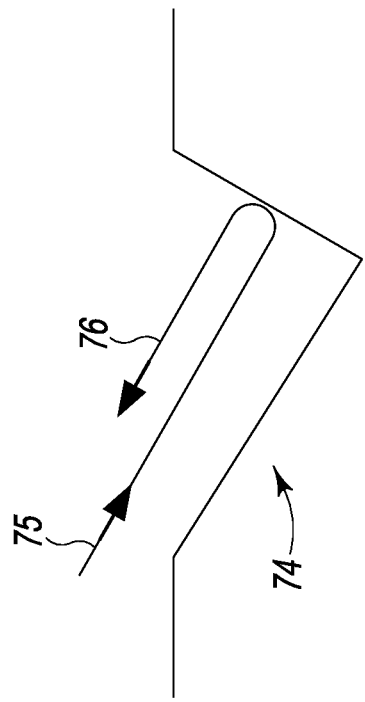
FIG. 7 is another alternative groove shape that may be used in embodiments of the present invention.

FIG. 7 shows another alternative groove shape 74 that may be used in other embodiments of the present invention. In FIG. 7, a two-surface "tipped" or angled groove 74 is used instead of the three-surface "box" groove of FIG. 5A. The "tipped" or angled groove 74 is still effective for reflecting ultrasonic waves 76 back to the transducer in response to a transmitted ultrasonic wave 75 to indicate the presence or absence of the groove 74.

In the preferred embodiments each transducer is provided at a fixed and known distance from the surface of the object to be read. For example, distances of about 2.5 inches have been effective in testing to date. In other embodiments each transducer may be provided at a variable distance from the object, with the distance preferably being within a narrow distance range.

Similarly, in the preferred embodiments each transducer is provided at a fixed and known angle relative to the surface of the object to be read. Angles much less than 90° are shown in the example of FIG. 5A to ensure the desired effect of having waves that do not encounter a groove to be reflected away from the transducer. In the illustrated embodiment, the angle is approximately 45° when measured from the surface over which the beam travels (i.e., from the left in FIG. 5A). Angles of between 30° and 60° may be used in other embodiments, depending on the configuration, the spacing of the grooves in the code, and the distance between the transducer and the grooves. Angles approaching 90° may also be used. In some embodiments the transducer provides a beam that strikes the grooved surface at an angle of less than 80°, and preferably less than 70°.

As previously indicated, the groove pattern is chosen to have "start" and "stop" grooves present with additional grooves either occurring or not occurring at a fixed interval between the end grooves. This allows the echo time spacing to vary widely with temperature, pressure or when being disturbed by incident air currents. The digitized echoes can be processed by a computer to time align the disturbed or varied echo arrivals which can then be averaged over time to provide a high signal noise ratio for robust identification.

The pattern of grooves may be provided in the surface of the object to be identified by any method effective for providing grooves. For example, laser etching may be used. Groove depths of approximately 0.025" have been successfully tested in the example shown, however this could be smaller or significantly larger depending on the needs of a particular application.

The pattern of grooves may be used to identify the object in which the grooves are provided, or any characteristic or feature of the object. For example, the grooves may be used to identify the type or model of a warhead, or any feature or characteristic of the warhead. For a complete discussion regarding methods, device, systems that implement the above, reference is made to US Patent Publication No. 2012/0182833 A1 of Jul. 19, 2012, the entire contents of which is specifically incorporated herein by this reference.

Though the described application for operation in air, the present invention may also be used in other media, such as drilling mud or nuclear reactor coolants (liquid sodium or lead bismuth eutectic). It can also be employed effectively in a contact mode.

In some preferred embodiments the transducer used in the device has a front face that is a good intermediate impedance match between air and the composite element. Moreover, it is preferred in some embodiments that this front face is heat and name blast resistant. These attributes are particularly valuable when the device is to be used to identify missiles or rockets to be launched from a military aircraft.

Among the other potential applications that are envisioned are:
  Security systems, particularly where the II) tag pattern must be hidden. If necessary the tag can be read from the back side of the pattern.
  Down hole applications, where drilling mud obscures an object visually.
  Identifying the fuel assemblies in a liquid metal cooled nuclear reactor. The opaque coolant prevents visualizing the fuel assemblies as well as all other internal components. Ultrasonic imaging may be used to read the ID numbers from a visual image of the fuel assembly handling socket. That may be backed up by a binary code machined into the rim of the socket that is read by a "clicker" on the fuel handler.
  Identifying the authenticity of replaceable components for medical devices, including but not limited to IV or integral feeding pumps.
  Identifying the authenticity of replaceable components for host systems that interact with replaceable components via ultrasonic wave.

In another embodiment of the invention, presence of an authentic disposable component involves use of soft elastomeric couplant materials that enable ultrasonic coupling to a cassette feature and thus enabling low cost detection of cassettes by using ultrasonics. A typical prior art medical IV tubing set 20 is shown in FIG. 1. The tubing set 20 typically includes an IV bag 21 that contains a liquid medicine to be dispensed, a tubing cassette portion 22, a first tube 23 that connects the bag 21 to the tubing cassette portion 22, a second tube 24 that connects a dispensing piece 25 with the tubing cassette portion 22. The tubing cassette portion 22 is a replaceable component.

Figure 2:
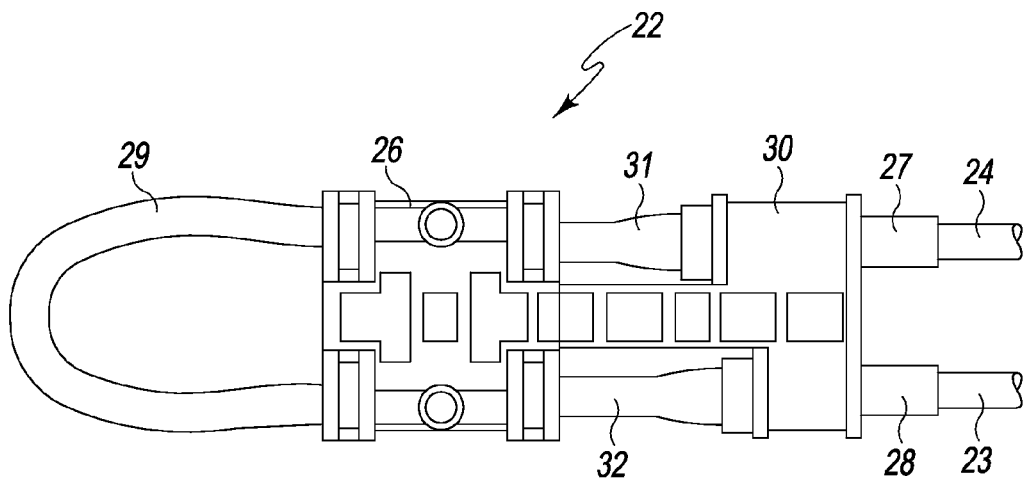
FIG. 2 is a plan view of the prior art tubing cassette of the prior art medical IV tubing set of FIG. 1.

The tubing cassette portion 22 is shown in greater detail in FIG. 2. The tubing cassette portion 22 includes an inlet 28 that is attached to the first tubing 23 and an outlet 27 that is attached to the second tubing 24, the inlet 28 and the outlet 27 fashioned within a first component 30. The inlet 28 is in communication with a first connecting tube 32 that extends into a second component 26 and into a loop tube 29. The loop tube 29 is in communication with a second connecting tube 31 via the second component 26. The second connecting tube 31 is in communication with the outlet 27 via the first component 30. The cassette portion 22 provides a replaceable component.

The plastic cassette portion 22 is shaped to be received and held by the receptacle of a pump.

Figure 3:
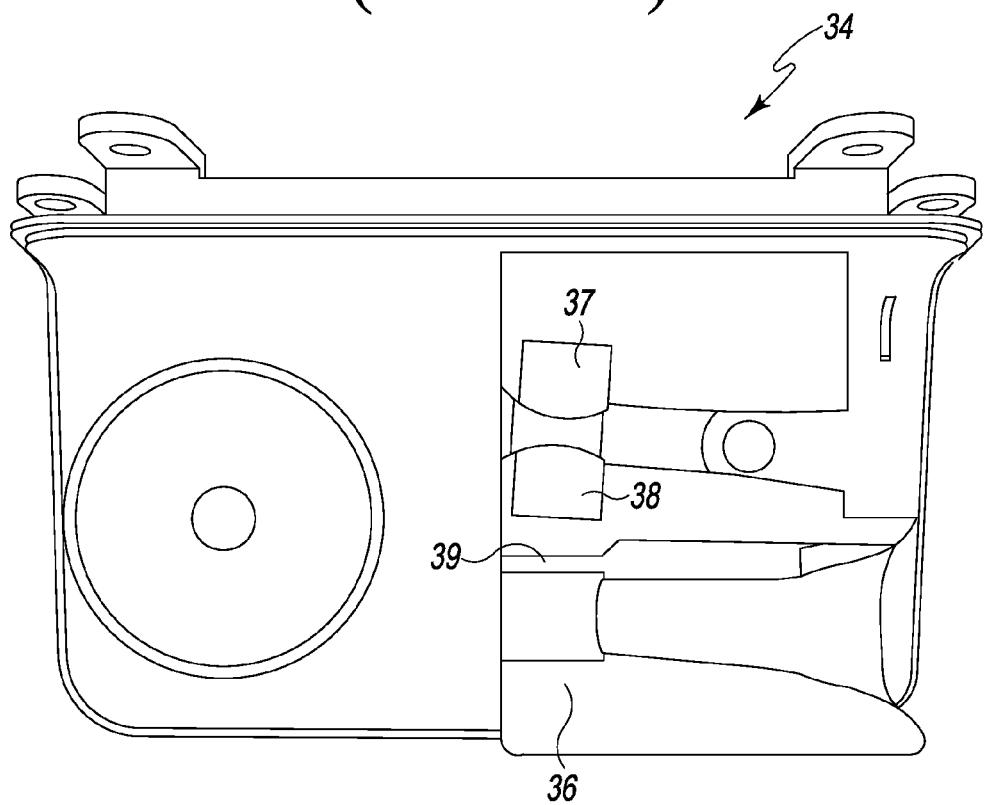
FIG. 3 is a plan view of a prior art medical pump/host system for use with the prior art medical IV tubing set of FIG. 1, and particularly, the prior art tubing cassette thereof.

A representative pump/host system 34 having a receptacle for a cassette portion 22 is shown in FIG. 3. When held in the pump 34, a pair of lugs 37, 18 extends from the pump 34 on either side of a portion of the tubing. Optionally, these lugs 37, 38 may include an ultrasonic transmitter and receiver, respectively, to obtain information regarding liquid flowing through the tubing. In some cases, as further described below, the pump may have two pairs of extending lugs 36, 39 so that the fluid on each side of the loop may be monitored.

Figure 8A:
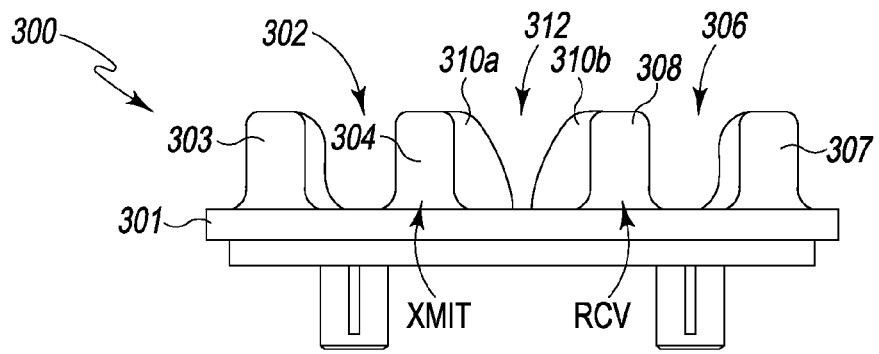
FIG. 8A is an illustration of an embodiment of the invention using elastomer components for the host system to create a void.
Figure 8B:
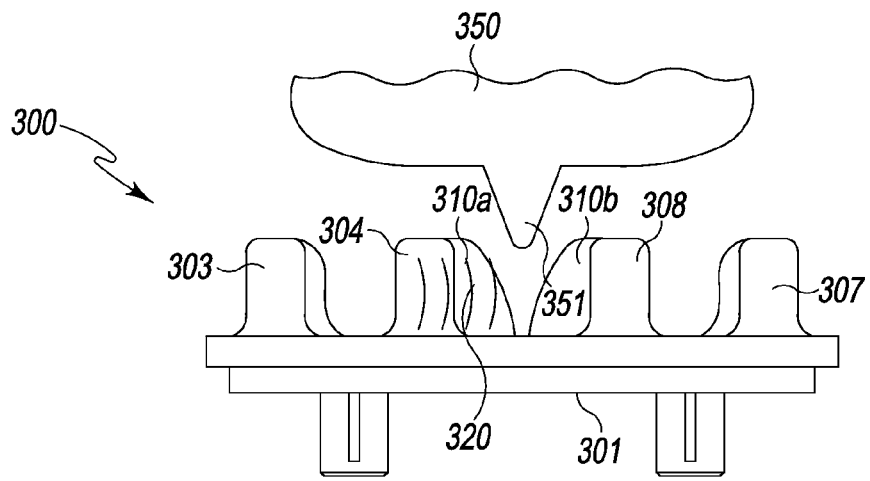
FIG. 8B is an illustration of the embodiment of FIG. 8A ready to receive a key feature of a replaceable component (cassette) and showing an ultrasonic signal being sent from an ultrasonic transmitter but not being received by an ultrasonic receiver because of the void.
Figure 8C:
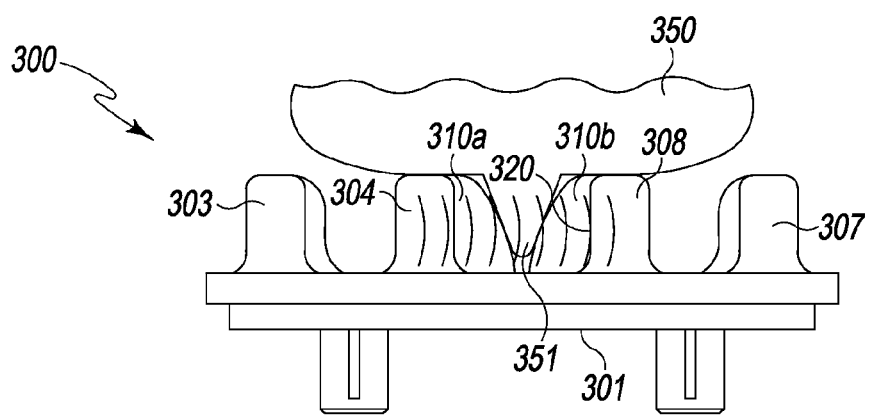
FIG. 8C is an illustration of the embodiment of FIG. 8A receiving the replacement component wherein the ultrasonic receiver is able to receive the transmitted ultrasonic signal through the elastomer components and the cassette key that fills the void.

In one embodiment of the invention, a soft elastomeric material is molded onto an infusion pump between an ultrasonic transmitter and an ultrasonic receiver, leaving a narrow gap of specific size and shape. When a suitable tubing cassette with a matching mechanical feature is installed into the pump, the feature completes an acoustic pathway. The soft elastomer ensures acoustic coupling FIGS. 8A-C illustrate this concept, wherein the transmitter (XMIT) and receiver (RCV) transducers form a part of the receptacle of the host infusion pump.

This system allows the transducer and elastomer components to be included with the host system. As the host system is usually more expensive that the replaceable component, the costs for replacement components can be kept to a minimum.

The present system can be retrofitted to existing pumps because only the elastomer between the middle transducer need be added. For example, in FIGS. 5A-C, each upwardly projecting lobe 304, 308 of the tube lobe pairs 303, 304 and 307, 308 that extend from a base 301) of the receptacle includes an ultrasonic transducer. One portion of tubing is placed between the left pair of lobes 303, 304 within the gap 302 formed thereby, and a different portion of tubing is placed between the right pair of lobes 307, 308 within the gap 306 formed thereby. During normal monitoring of the tubing cassette, each pair of transducers ultrasonically detects characteristics of the tubing and/or fluid flowing within the tubing. However, the two middle transducers XMIT, RCV can be separately activated to detect the replaceable cassette. For example, the manufacturer may begin to sell high quality tubing cassettes 350 having the downwardly projecting plastic key 351 that fits between the elastomeric components 310a and 310b. Older, low-quality cassettes will not have this key, but may still be held by the receptacle. If a completed ultrasonic circuit (represented by the waves 320) is detected by the host pump, it may be assumed that an authorized, high quality cassette is being used with the host pump. If no ultrasonic circuit is detected, it may be deduced that either the tubing cassette is missing completely, or else that a low-quality cassette is being used, and a fault notification may be generated.

It will be appreciated that the disclosed design may be retrofitted to existing AIL pumps. For example, the transmission/detection of the ultrasonic wave or signal between the middle pair of transducers could be accomplished merely by altering the software used to drive the transducers and read the resulting received waveform. The host pump receptacle may be retrofitted with the elastomer by providing appropriate shaped elastomeric elements, and adhesively adhering them to the projecting lugs.

Figure 9A:
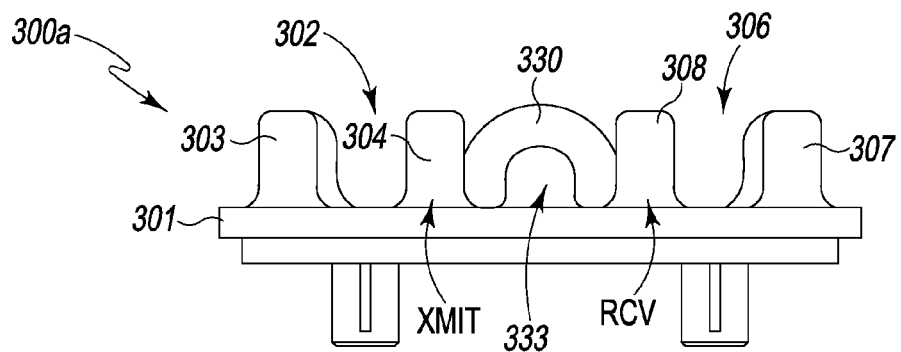
FIG. 9A is an illustration of an embodiment of the invention using a bowed elastomer component for the host system to create a void.
Figure 9B:
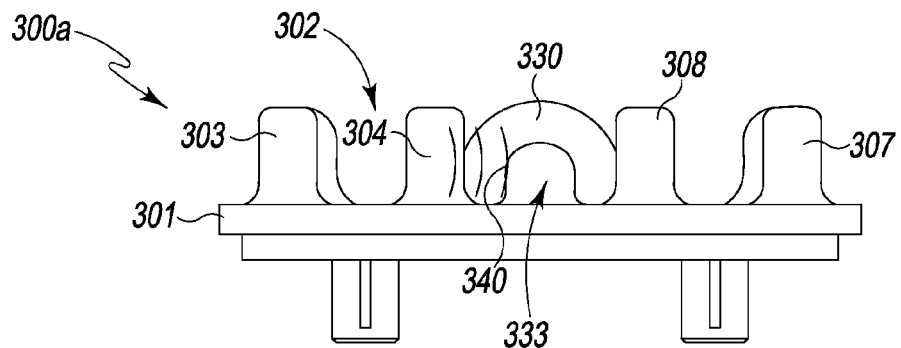
FIG. 9B is an illustration of the embodiment of FIG. 9A, with the ultrasonic signal from the ultrasonic transmitter not reaching the ultrasonic receiver due to the void.
Figure 9C:
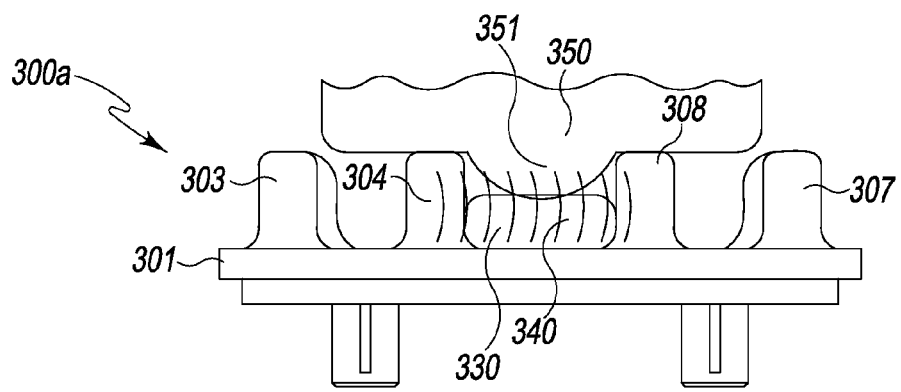
FIG. 9C is an illustration of the embodiment of FIG. 9A receiving the replacement component wherein the ultrasonic receiver is able to receive the transmitted ultrasonic signal through the elastomer component and the cassette key that tills the void.

Another embodiment uses a bowed elastomer shape and the directional properties of ultrasound to create a self contained acoustic path that is only enabled when interfaced by a cassette having a specified mating feature. For example, in the embodiment shown in FIGS. 9A-C, the acoustic path is disabled due to the air gap 333 formed by the bow of the elastomer 330.

When a replaceable component 350 is inserted, the key 351 of the replaceable component deforms 350 the elastomer 130 to thereby form an acoustic pathway 340 between the transmitter XMIT and the receiver RCV.

In another embodiment, depicted in FIGS. 10A-D, there could be a continuous pathway of elastomer 80 between the transmitter 81 (XMIT) and the receiver 82 (ROTE) when a replaceable component (e.g. cassette) is not present (FIG. 10A) However, the key 85 of the replaceable component (cassette) 84 could be comprised of a material that does not transmit ultrasonic waves, and shaped to squish the elastomer 80 to such a thin level 83 that it loses its effectiveness as an ultrasonic pathway 10C).

Figure 10C:
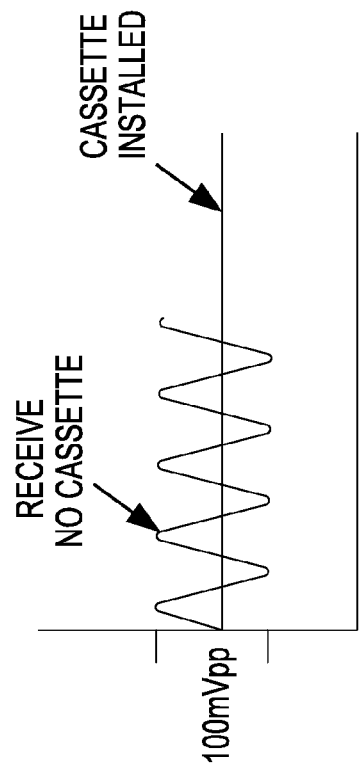
FIG. 10C is an illustration of the embodiment of FIG. 10A with a keyed cassette inserted therein, the key of the keyed cassette deforming the elastomer to block an ultrasonic signal emitted by the ultrasonic transmitter from reaching the ultrasonic receiver to indicate no cassette.
Figure 10D:
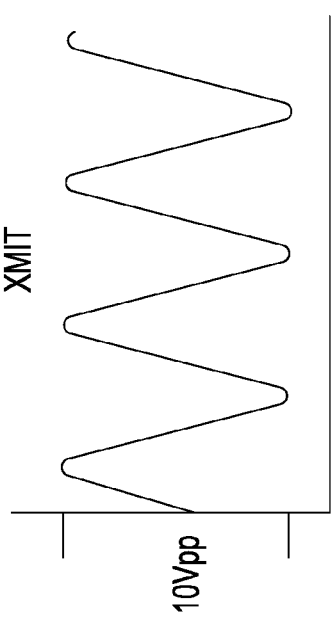
FIG. 10D is a graph of the ultrasonic signal showing that the ultrasonic signal is blocked by the deformation of the elastomeric by the key or the keyed cassette, (replaceable component) such that it does not reach the ultrasonic receiver.
Figure 10A:
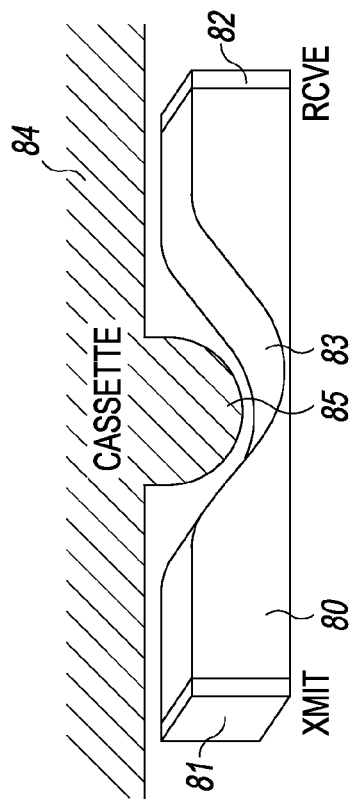
FIG. 10A is an illustration of another embodiment of the invention in which a continuous pathway of an elastomer is used between an ultrasonic transmitter and an ultrasonic receiver, the continuous pathway providing a signal pathway for a transmitted ultrasonic signal from the ultrasonic transmitter and the ultrasonic receiver to indicate no replaceable component (e.g. a keyed cassette) has been inserted therein.
Figure 10B:
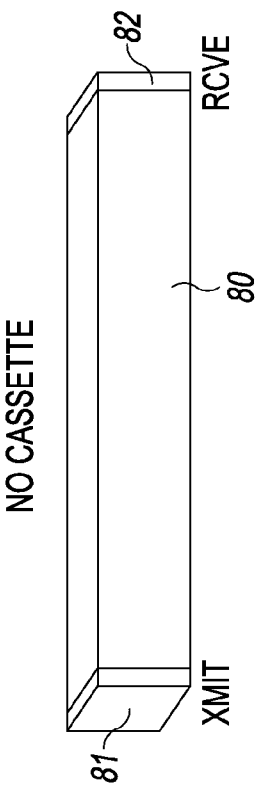
FIG. 10B is a graph of the ultrasonic signal as it travels from the ultrasonic transmitter to the ultrasonic receiver for the embodiment of FIG. 10A wherein no keyed cassette (replacement component) has been inserted.

In this case, the absence of the replaceable component (FIG. 10A) would be indicated by the presence of a received ultrasonic signal (FIG. 10B), and the presence of a replaceable component (FIG. 10C) is indicated by the absence of an ultrasonic signal (FIG. 10D).

Figure 11B:
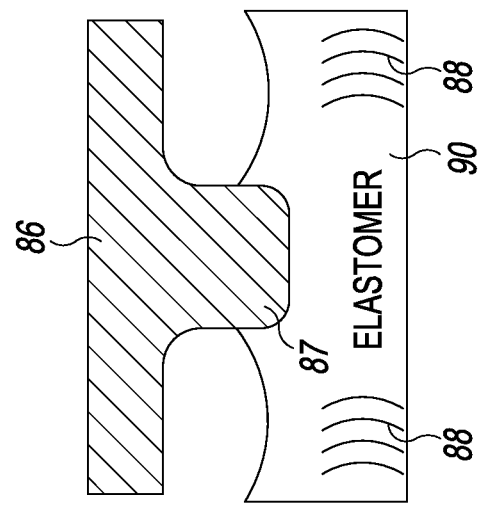
FIG. 11B is an illustration of the receipt of the keyed cassette (replaceable component) in the configured elastomer (host), wherein the cassette key deforms the elastomer to allow an ultrasonic signal to transit through the elastomer from one side (a transmit side) to the other side (a receive side).
Figure 11A:
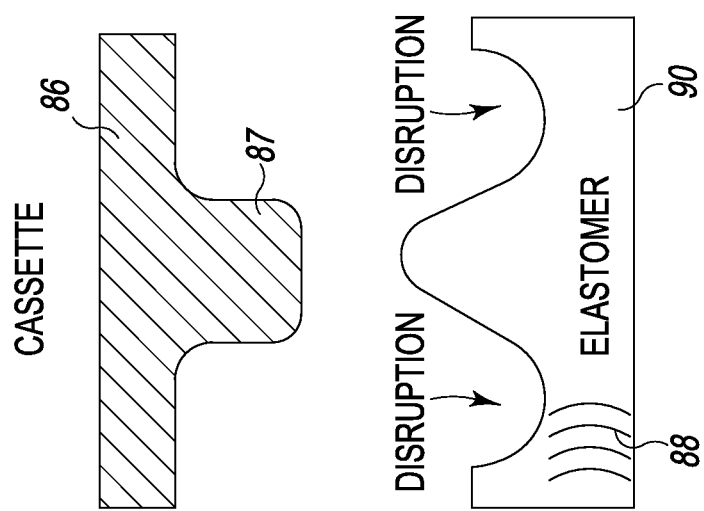
FIG. 11A is an illustration of another embodiment of the invention wherein an elastomer is configured to naturally provide disruptions in transit of an ultrasonic signal through the elastomer, a keyed cassette (replaceable cassette) is shown ready for insertion into the elastomer.

Another embodiment, depicted in FIGS. 11A-B, is to shape the elastomeric material 90 and the key 87 of the cassette (replaceable component) 86 so that the presence or absence of a key 87 results in a desired presence or absence of an ultrasonic pathway. FIG. 11A depicts the elastomer 90 with two ultrasonic signal disruption configurations between a hump. The ultrasonic signal disruption configurations do not allow the transmitted ultrasonic signal 88 to reach the other side of the elastomer 90. The system then knows that a cassette has not been installed since no ultrasonic signal reaches the end of the elastomer 90 (which includes the receiving ultrasonic transducer, not shown). As depicted in FIG. 11B, when the cassette 86 is inserted against the elastomer 90, the key 87 compresses the hump of the elastomer 90. Compression of the hump causes the disruption features to be in a non-disruption mode thereby allowing the ultrasonic signal 88 to reach the end of the elastomer 90. The system then knows that a cassette has been installed since an ultrasonic signal does reach the end of the elastomer 90 (which includes the receiving ultrasonic transducer, not shown).

Figure 12:
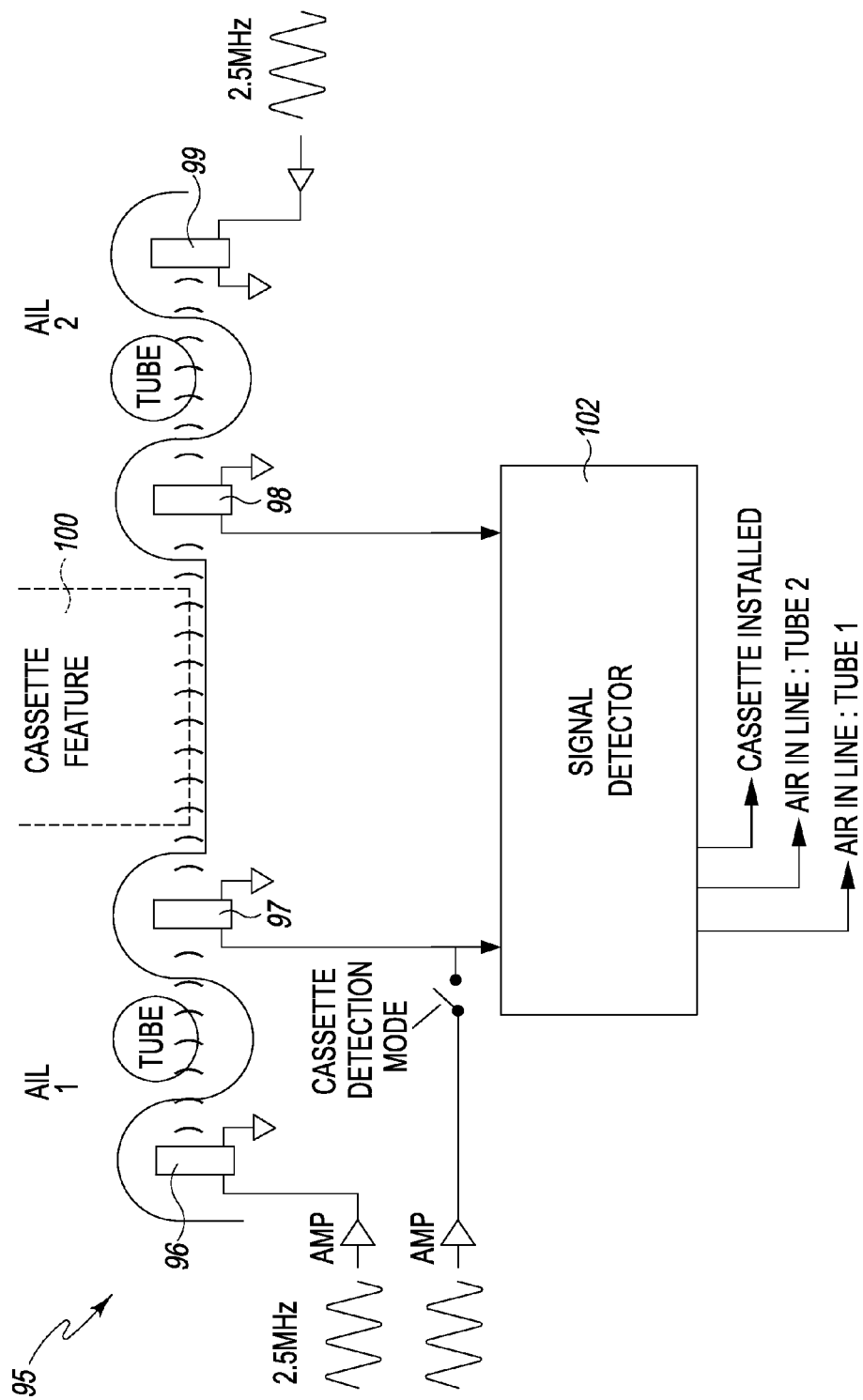
FIG. 12 is a schematic of a system for detecting the presence or absence of a cassette with a feature e.g. key) in accordance with the present principles (i.e., replaceable component), particularly in connection with the tubular delivery of a liquid (e.g. a medical IV pump system).

A schematic of a system 95 for detecting the presence or absence of a replaceable component (e.g. cassette) for a dual tube system, and additionally for determining whether there is air in the tubing/line (AIL), is shown in FIG. 12. The system 95 includes a first air in line reader AIL1 having an ultrasonic transmitter 96 and an ultrasonic transducer 97 serving as a receiver for the AIL 1. A tube is shown situated between the transmitter/receiver pair 96, 97. The system 95 further includes a second air in line reader AIL 2 having an ultrasonic transducer 98 serving as a transmitter for the AIL2 and an ultrasonic receiver 99. A tube is shown situated between the transmitter/receiver pair 98, 99. A signal detector 102 receives a signal from the receiver 97 which processes the signal to determine the presence or absence of air in the tube. An amount of air within the tube/line may also be determined. The signal detector 102 also receives a signal from the receiver 99 which processes the signal to determine the presence or absence of air in the tube. An amount of air within the tube/line may also be determined. The system 95 also determines whether there is an installed cassette/cassette feature (replaceable component) 100. The transducer 97 transmits a signal that may or may not be received by the receiver 98 depending on whether a cassette is installed or not (presence or absence of the replaceable component). The signal detector 102 processes the signal to determine the presence or absence of a cassette.

The left-most transducer 97 and the right-most transducers 98 are thus configured to transmit ultrasonic waves. The second transducer can be configured to either receive or transmit an ultrasonic wave. During tube/cassette detection mode, it acts as a receiver. In cassette detection mode, it operates as a transmitter, and its signal is received by the third transducer. All received signals are processed by the signal detector 102 of the host system 05. Thus, it will be appreciated that the transducers operate to both detect fluid in tubes, and to detect and/or identify the tubing cassette/replaceable component. An alternative to an elastomeric couplant may be a deformable fluid filled vessel.

While the present discussion and the figures show host system receptacle components in which the tubing cassettes receive two tubes, some pumps operate in connection with a cassette that utilizes only a single tube, and therefore, which has only two projecting lugs Examples of these pumps are provided in FIGS. 4A-C. FIG. 4A shows a configuration 40 in which a single pair of lugs 42a, 42b extend from a base 41 to define a tube reception area 43. FIG. 4B shows a configuration 46 in which a single pair of lugs 48a-48b extend from a base 47 to define a tube reception area 49. FIG. 4C shows a configuration 50 in which a single pair of lugs 53a, 53b extend from a base 51 to define a tube reception area 52.

Such prior art receptacles as depicted in FIGS. 4A-C may be modified to add a third lug containing a piezoelectric transducer, and a corresponding elastomer between the second and third lugs. For such embodiments involving elastomers, the ultrasonic signal/wave may generally be in the range of 1 MHz-6 MHz. While frequencies outside this range will also work, 2.5 MHz is suitable.

In another embodiment, multiple sets of transducer-pairs may be provided, and the various combinations of extending keys from the replaceable component may be provided. This allows number and placing of lugs to constitute a code allowing the model number or serial number (or other data) of the replaceable component to be identified. For example, four sets of the following transducer pairs as follows could be provide, in this view, essentially stacked from front to back, identified herein as, 1, 2, 3 and 4.

If no replaceable component is present, there would be no keys to depress the elastomer, so none of the four pairs would receive an ultrasonic signal. This would result in a logical reading for the four pairs of 0, 0, 0, 0. Different replaceable component types could have different combinations of projecting keys For example, a tubing cassette with ⅛" tubing could have a lug at position 1, ¾" tubing could have a lug at position 2, ⅜" tubing at positions 1 and 2, and so on. The number combinations identifiable would be $2^n$ where n is the number of transducer pairs. For example, if 16 pairs were used, 65,536 variations are possible. Depending on the number of replaceable components, this could allow a particular combination of keys incorporated into a replaceable component to represent a not just a model number or size, but a unique serial number.

Figure 13:
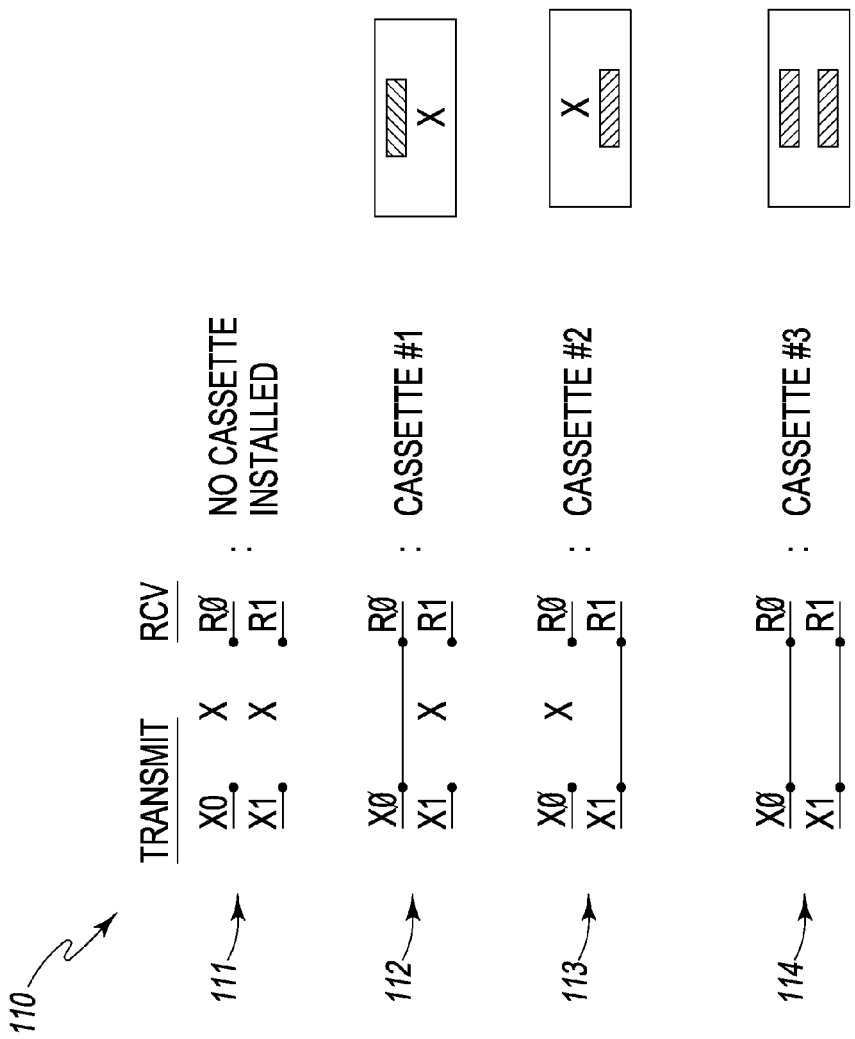
FIG. 13 is a chart illustrating the concept of using multiple sets of transducer (transmitter-receiver) pairs, particularly two sets of transducer pairs wherein the various combinations may comprise a code for data associated with a replaceable component.

A chart 110 showing this concept of just two pairs of transducers—a transmitter and a receiver (X0, R0 and X1, R1) is shown in FIG. 13. As shown in the chart 110, when both the first transducer pairs X0, R0 and X1, R1 do not receive a signal, 111, no cassette has been installed. When the first transducer pair X0, R0 receives a signal but the second transducer pair X1, R1 does not receive a signal, 112, cassette #1 has been installed. When the first transducer pair X0. R0 does not receive a signal but the second transducer pair X1, R1 does receive a signal, 113, cassette #2 has been installed. When the first transducer pair X0, R0 receives a signal and the second transducer pair X1, R1 receives a signal, 114, cassette #3 has been installed.

An alternate method of identifying a replaceable component is to have the key or mechanical feature of the replaceable component transmit varying leek of ultrasonic energy which could be used to identify the tube set. For example a key comprised of a material that reliably transmits 100% of the ultrasonic energy can represent one version or size of a replaceable component. If the key transmits transmission of 75% of the energy, it could represent a second version of a replaceable component, etc. These variations can be accomplished by selecting the type of plastic used to comprise the key, or, the height of the key, causing the key to compress the elastomer material to different extents. Moreover, the idea of keys/elastomeric combinations that allow transmission of different levels of energy can be combined with the above concept of having multiple pairs of transducers, to increase the number of individually identifiable types of replaceable components.

Figure 14:
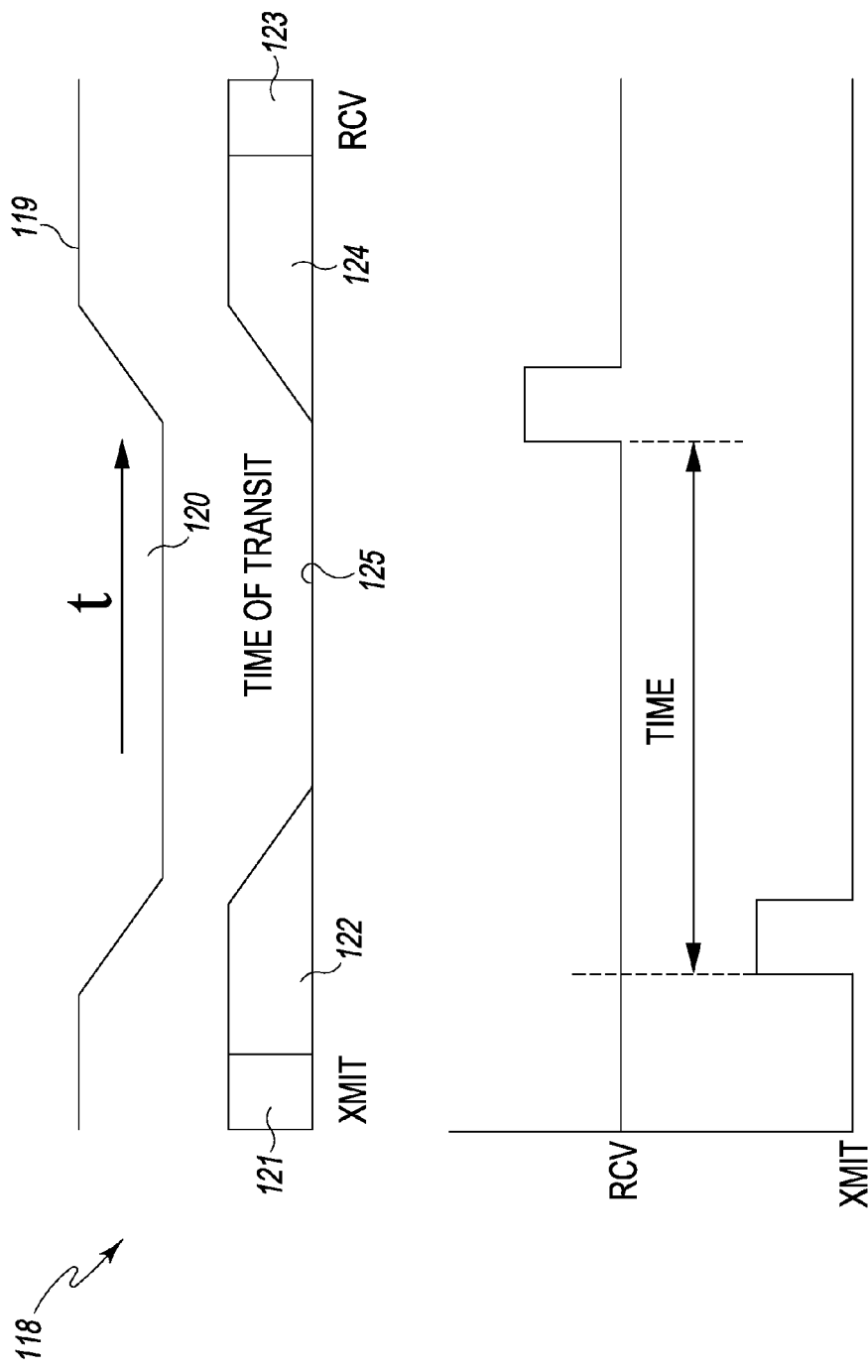
FIG. 14 provides another embodiment of the invention and an associated graph, wherein time of flight of an ultrasonic signal between an ultrasonic transmitter and ultrasonic receiver is measured for a replaceable component having a feature of a material that provides different velocities (speeds) of sound through the material to identify different cassettes.

In addition, keys of different materials that have different sound speeds (velocity) for ultrasonic waves can also be used to distinguish among different types of replaceable components. This concept is shown in FIG. 14 which depicts another embodiment of the invention 118 and an associated transmit and receive graph, wherein time of flight of an ultrasonic signal between an ultrasonic transmitter 121 and an ultrasonic receiver 123 is measured for a replaceable component 119 having a feature 120 of a material that provides different velocities (speeds) of sound through the material to identify different cassettes. The device includes separated elastomers 122, 124 and a gap 125 between the two. If no cassette key 120 is situated between the elastomers 122, 124, no ultrasonic signal can reach the receiver 123. If the cassette key 120 is provided, the signal reaches the receiver 123.

Another way of identifying a replaceable component is, in lieu of using a transducer transmitter and receiver having a direct (linear) pathway, to transmit a pulse signal in the direction of a replaceable component, and then wait to see whether a reflected (echo) signal is received. In this embodiment, shown in FIG. 15, since the ultrasonic, wave may be transmitted through air, it may be desirable to have a couplant over the transducer that interfaces with the air to minimize impedance mismatch issues. Such a couplant may be, for example, a silicon gel, or an elastomer, with or without hollow glass beads.

Figure 15:
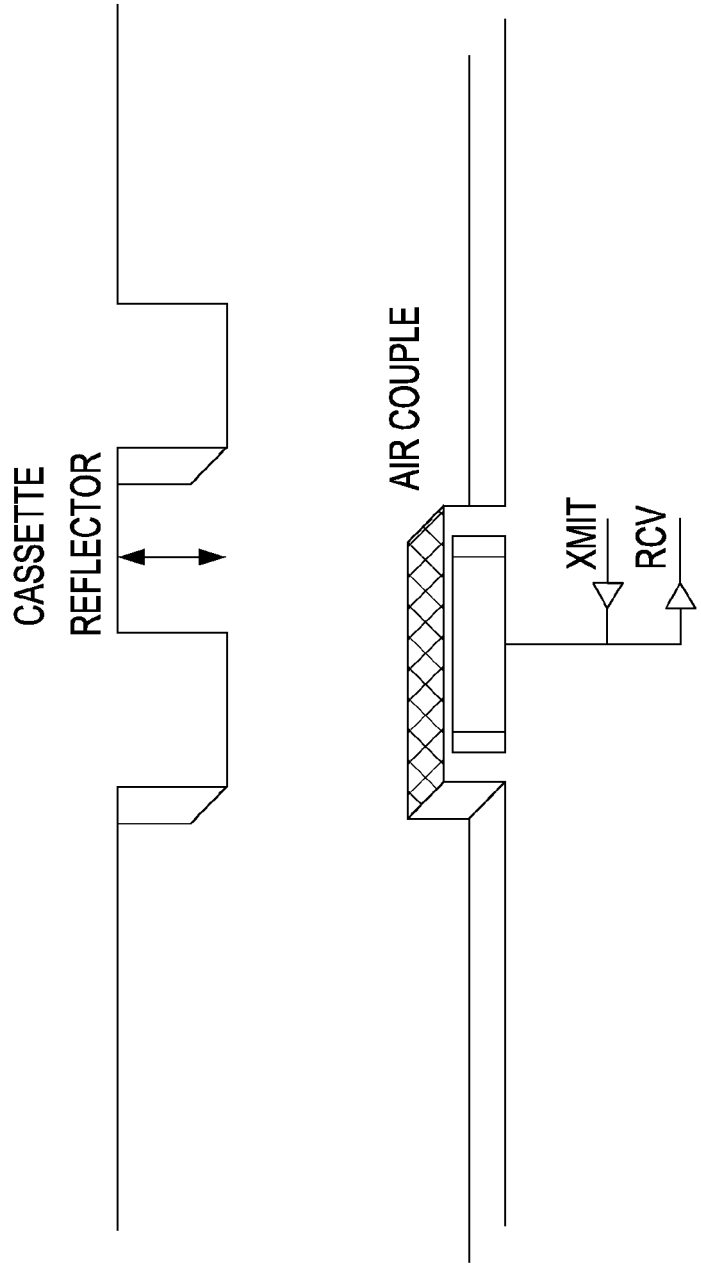
FIG. 15 is an illustration of another embodiment of the invention wherein the same ultrasonic transducer is used for both transmitting an ultrasonic signal and listening for the ultrasonic reflection.
Figure 16:
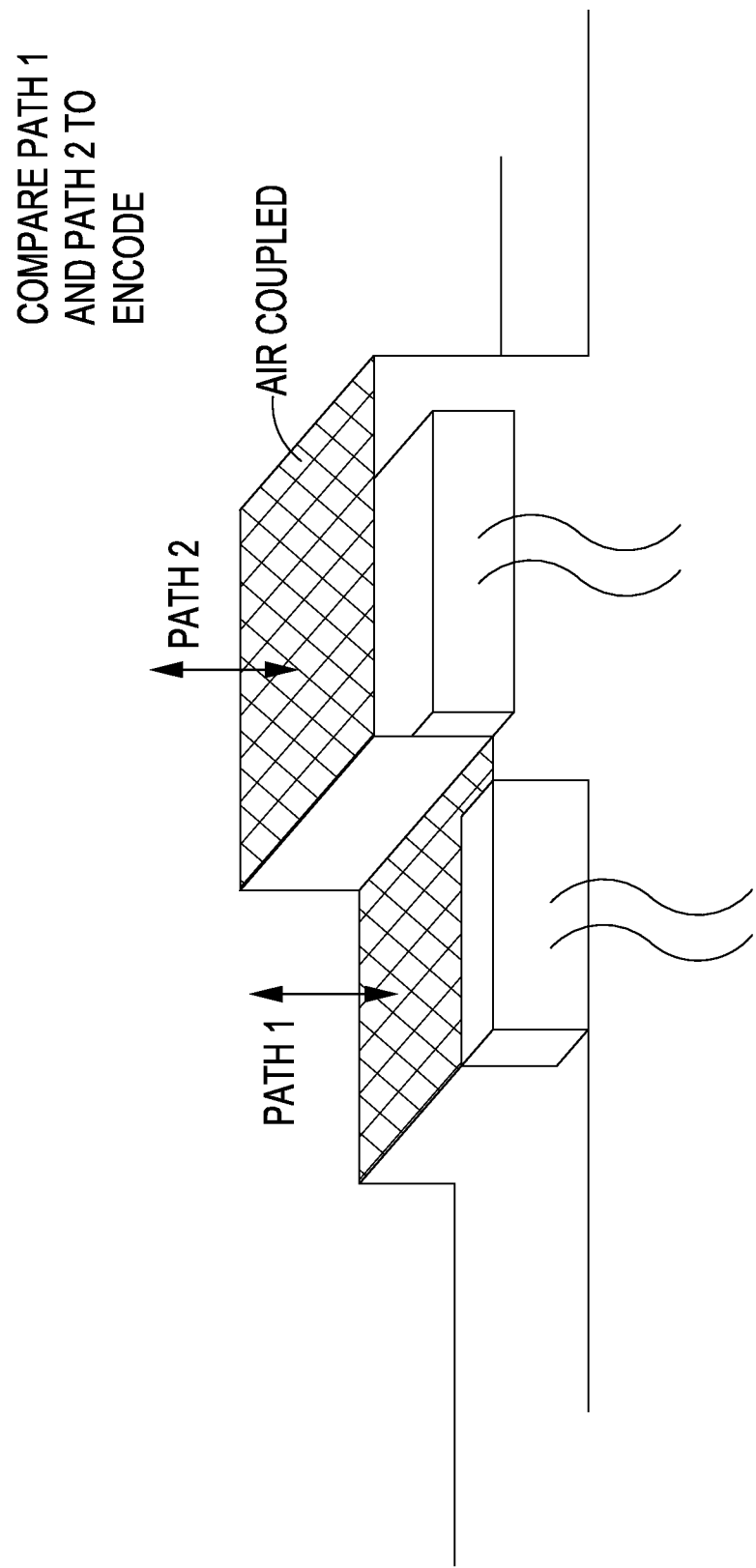
FIG. 16 is an illustration of an array of spaced reflective surfaces for encoding characteristics and/or model/serial number of a replaceable component.
Figure 17:
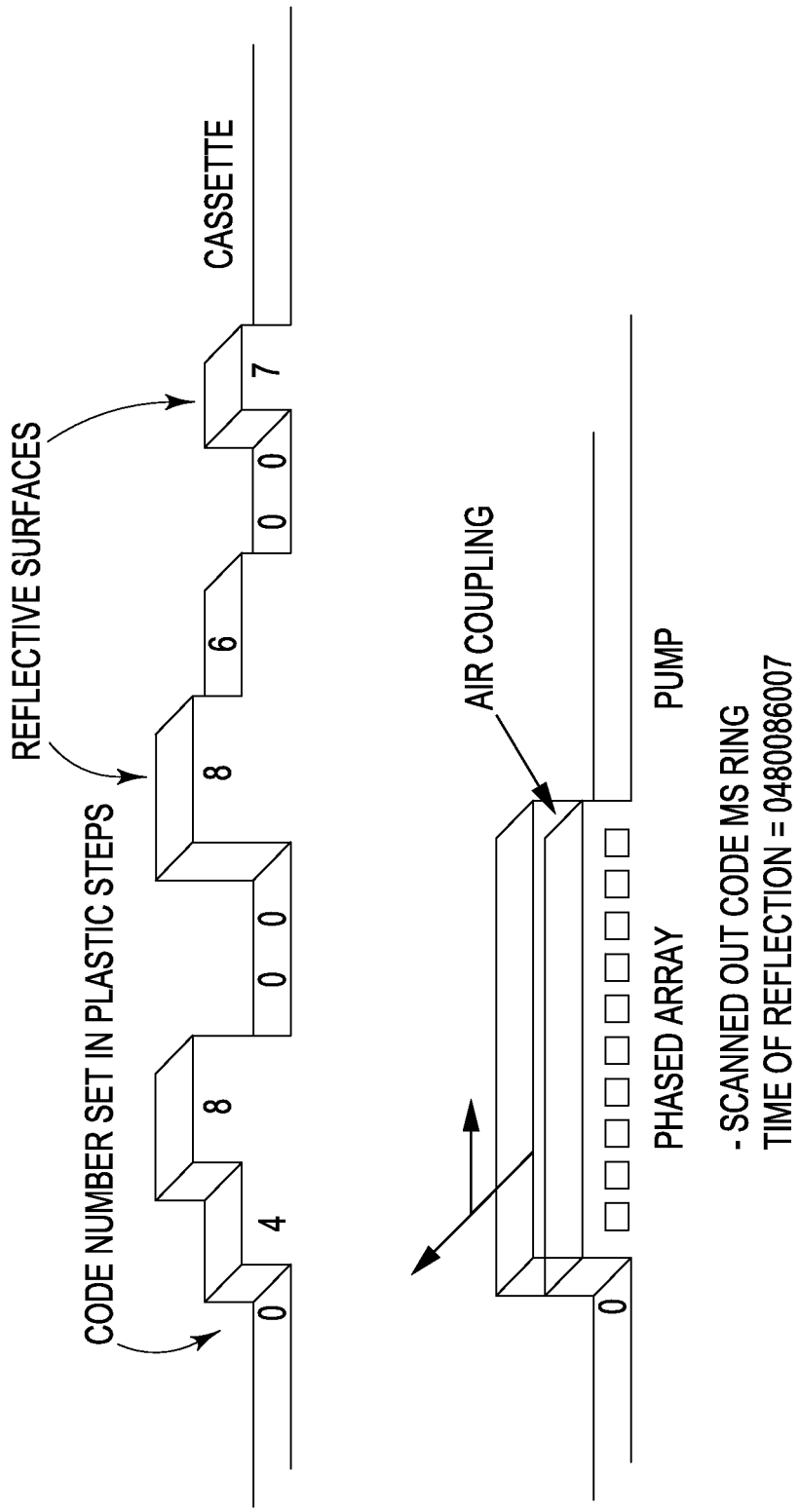
FIG. 17 is a further illustration of an array of spaced reflective surfaces for encoding characteristics and/or model/serial number of a replaceable component.

In another embodiment shown in FIG. 15, the same transducer may be used to both transmit the ultrasonic pulse, and then listen for the reflection. As with the previous embodiment, multiple transducers may be stacked, and the replaceable component can be provided with configured to either have or not have a reflecting surface over specific transducers, to allow a variety of different types of replaceable components to be identified by model number or serial number. In addition, an additional method, FIG. 16, for identifying replaceable components is to vary the distance of the surface of the replaceable component that reflects a signal, and then measure the time required to receive the reflected signal. For example, a replaceable component may be configured so that when it is received by the receptacle of the host system, its reflective surface from the host's transducer is either abuts the transducer, or is spaced, 1, 2, 3 or 4 millimeters (or some other varying distance) from the transducer. In addition, multiple transducers may be arrayed, and multiple, spaced reflective surfaces may be provided on the replaceable component to further encode the characteristics or model/serial number of the component. See, for example, FIG. 17

Figure 18:
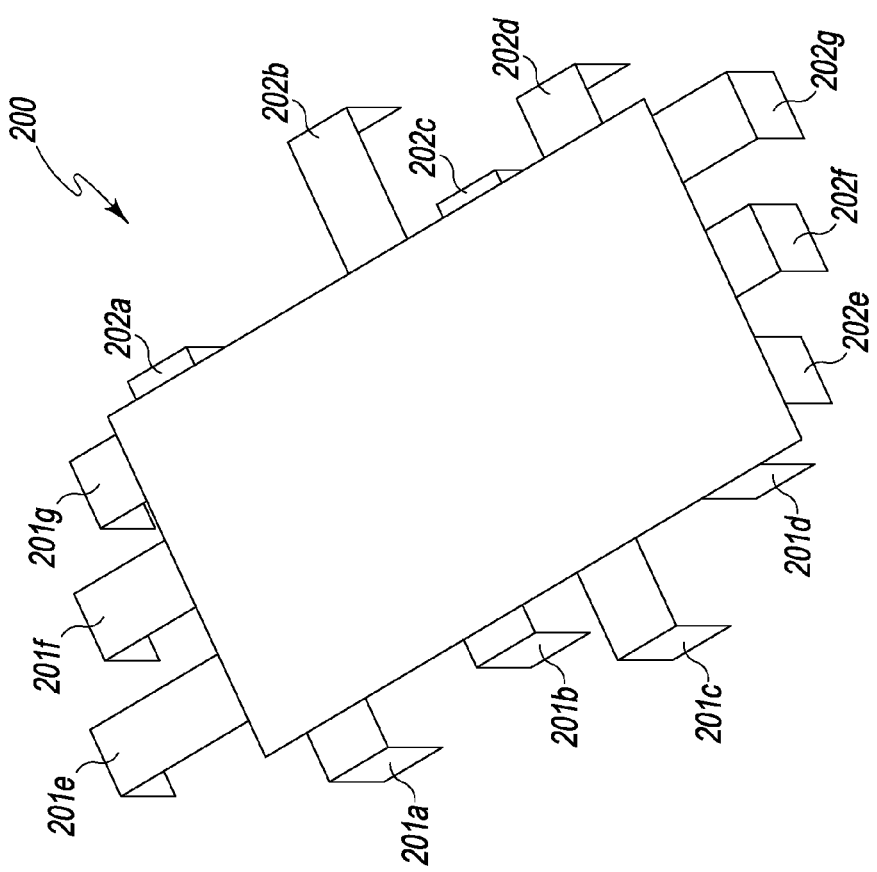
FIG. 18 is an illustration of an exemplary embodiment of a replaceable component having surfaces in various dimensions to provide unique ultrasonic wave form signatures, the surfaces defining flanges configured with an ultrasonic transducer (transmitter, receiver, or both) to provide transmitted and reflected ultrasonic signals.

It will be appreciated that in the above figure, "pump" may refer any type of a host system, and "cassette" refers to any type of replaceable component. The above shows varying depths of the vertical "height" of surfaces of the replaceable component However, the replaceable components may be provided with surfaces in other dimensions that provide unique ultrasonic reflected wave form signatures. For example, the belt embodiment has flanges on the left, right, front and rear edges that extend varying distances from the central body of the replaceable component. The host system may be configured with a transducer for each flange position. Such is presented in FIG. 18 wherein a replaceable component 200 is shown having various pairs of transmitter/receiver pairs 201a-g, 202a-g.

Of course, as shown above, the bottom surface of the replaceable component (not visible) may also have surfaces of varying heights in areas that correspond to, and reflect signals from, specific transducers of the host system. It is also possible for there to be one or more holes in the top surface over particular, and in this view, upwardly-projecting, transducers. The corresponding transducer underneath a hole would not detect a reflected wave.

In addition, a phased array arrangement may be used to provide reduce the number total number of transducers required and/or to obtain more precise readings of distances to surfaces of the replaceable component.

What is claimed is:

1. A tubing cassette for medical pump, in which the medical pump comprises a receptacle for receiving the tubing cassette, an ultrasonic transmitter and an ultrasonic receiver spaced from the ultrasonic transmitter, the tubing cassette comprising:
 a cassette body having:
  means for being retained by the medical pump, and structure for holding tubing; and
  and wherein the cassette is operable to alter ultrasonic wave communication between the transmitter and receiver when the tubing cassette is retained by the medical pump.

2. The tubing cassette of claim 1, further comprising a key projecting from the cassette body, the key being operable to alter ultrasonic wave communication between the transmitter and receiver when the tubing cassette is retained by the medical pump.

3. The tubing cassette of claim 1 wherein the means for being retained by the medical pump is shaped to be retained by a medical pump selected from the group of IV infusion pumps, dialysis machines, microplate dipensers, peristalic pumps, reagent dispensers, arthroscopy pumps and laproscopic irrigation systems.

4. A tubing cassette for medical pump, in which the medical pump comprises a receptacle for receiving the tubing cassette, a plurality of sets of an ultrasonic transmitter and an ultrasonic receiver spaced from the ultrasonic transmitter, the tubing cassette comprising:
 a cassette body having:
  means for being retained by the medical pump, and structure for holding tubing; and
  a plurality of means for altering ultrasonic wave communication between a transmitter and receiver when the tubing cassette is retained by the medical pump.

5. A method for identifying a replaceable component for a host system having a receptacle for the replaceable component and a piezoelectric transducer comprising:
  a) providing a pattern of grooves on the surface of the replaceable component, the pattern of grooves indicating a characteristic of the replaceable component;
  b) placing the replaceable component in the receptacle of the host system;
  c) emitting an ultrasonic wave from the piezoelectric transducer toward the pattern of grooves, wherein the wave encounters the pattern of grooves at an angle of less than 90° so that waves striking the interior of a groove are reflected back to the transducer as echo waves, while waves not striking the interior of a groove are reflected away from the transducer, and
  d) reading the pattern of returning echo waves to determine the characteristic of the replaceable component indicated by the pattern of grooves.

6. The method of claim 5 wherein the grooves on the surface of the replaceable component are parallel.

7. The method of claim 5 wherein the replaceable component comprises a projectile.

8. The method of claim 5 wherein the replaceable component comprises a cassette capable of holding tubing.

9. The method of claim 5 wherein a liquid or mud is between the transducer and the grooves.

10. A method for identifying a characteristic of a replaceable component for a host system, comprising:
  a) providing a host system having
    a replaceable component receptacle,
    a piezoelectric transmitter,
    a piezoelectric receiver spaced from the transmitter, and
    wherein the receptacle is shaped to receive a replaceable component having a key that is positioned within the space between the transmitter and receiver when the replaceable component is received by the receptacle;
  b) emitting an ultrasonic signal from the transmitter; and
  c) detecting whether the emitted ultrasonic signal is received by the receiver.

11. The method of claim 10 further comprising the step of measuring the time the emitted signal takes to travel from the transmitter to the receiver.

12. A method for determining the presence or characteristic of a replaceable component for a host system, comprising:
  a) providing a host system having
    a receptacle for a replaceable component;
    a piezoelectric ultrasonic wave transmitter,
    a piezoelectric receiver spaced from the piezoelectric transmitter, and
    means for comparing a received ultrasonic signal to at least one waveform signature;
  b) positioning the replaceable component in the receptacle;
  c) transmitting an ultrasonic wave from the transmitter toward the receiver;
  d) receiving the transmitted ultrasonic wave; and
  e) comparing the received ultrasonic wave to at least one waveform signature; and
  f) generating an output indicating the presence or a characteristic of the replaceable component based on the comparing step.

13. The method of claim 12 wherein the ultrasonic wave is altered when the replaceable component is in the receptacle.

14. The method of claim 12 wherein the replaceable component includes an elastomeric element that is positioned intermediate the transmitter and receiver when the component is in the receptacle of the host system.

15. The method of claim 12 wherein the host system further comprises:
  an elastomeric material intermediate the transmitter and receiver and through which ultrasonic wave passes; and wherein
  when the replaceable component is in the receptacle, it engages the elastomeric material to thereby alter the ultrasonic wave received by the receiver.

16. The method of claim 12 wherein the comparing step compares the wave form signature based on the time for the ultrasonic wave to travel from the transmitter to the receiver.

17. The method of claim 12 wherein the comparing step compares wave form signature based on the magnitude of the received waveform.

18. The method of claim 12 wherein the output indicates a model number of the replaceable component.

19. The method of claim 12 wherein the output indicates a serial number of the replaceable component.

20. A replaceable component for a host system, in which the host system comprises a receptacle for receiving the replaceable component, an ultrasonic transmitter and an ultrasonic receiver spaced from the ultrasonic transmitter, and an elastomer disposed between the transmitter and receiver and, the replaceable component comprising:
  a component body having means for being held by the receptacle of the host system,
  a key projecting from the body shaped to engage the elastomer of the host system to thereby alter its ultrasonic wave transmissive properties when the component body is being held by the receptacle.

21. The replaceable component for a host system of claim 20, wherein the key is operable to impede the transmission of ultrasonic waves between the transmitter and receiver when the component is in the receptacle.

22. The replaceable component for a host system of claim 20, wherein the key is operable to enhance the transmission of ultrasonic waves between the transmitter and receiver when the component is in the receptacle.

23. The replaceable component for a host system of claim 20, wherein the replaceable component comprises a tubing cassette.

24. A replaceable component for a host system, in which the host system comprises a receptacle for receiving the replaceable component, an ultrasonic transmitter and an ultrasonic receiver spaced from the ultrasonic transmitter, the replaceable component comprising:
  a component body having means for being held by the receptacle of the host system,
  an elastomeric key projecting from the body shaped to fill the space between the transmitter and receiver when the replaceable component is being retained in the receptacle, to thereby permit ultrasonic communication between the transmitter and receiver.

25. The replaceable component for a host system of claim 24, wherein the replaceable component comprises a tubing cassette.

* * * * *